(12) United States Patent
Hoshishima et al.

(10) Patent No.: US 8,885,165 B2
(45) Date of Patent: Nov. 11, 2014

(54) FLUORESCENCE DETECTING DEVICE AND FLUORESCENCE DETECTING METHOD

(75) Inventors: Kazuteru Hoshishima, Tamano (JP); Shigeyuki Nakada, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 742 days.

(21) Appl. No.: 13/145,763

(22) PCT Filed: Jan. 15, 2010

(86) PCT No.: PCT/JP2010/000201
§ 371 (c)(1),
(2), (4) Date: Jul. 21, 2011

(87) PCT Pub. No.: WO2010/084719
PCT Pub. Date: Jul. 29, 2010

(65) Prior Publication Data
US 2012/0029831 A1 Feb. 2, 2012

(30) Foreign Application Priority Data

Jan. 22, 2009 (JP) ................................. 2009-011565

(51) Int. Cl.
*G01N 21/25* (2006.01)
*G01N 21/64* (2006.01)
*G01N 15/14* (2006.01)

(52) U.S. Cl.
CPC .......... *G01N 21/6408* (2013.01); *G01N 15/147* (2013.01); *G01N 21/6428* (2013.01); *G01N 2021/6419* (2013.01); *G01N 2021/6421* (2013.01); *G01N 2021/6441* (2013.01)
USPC ........................................ 356/417

(58) Field of Classification Search
USPC .......................................................... 356/417
See application file for complete search history.

(56) References Cited

U.S. PATENT DOCUMENTS

| | | | |
|---|---|---|---|
| 2006/0108540 A1 | 5/2006 | Nakajima | |
| 2009/0012721 A1 | 1/2009 | Kimura et al. | |
| 2011/0278471 A1* | 11/2011 | Hoshishima | 250/459.1 |

FOREIGN PATENT DOCUMENTS

| | | | |
|---|---|---|---|
| JP | 2002-533658 A | 10/2002 | |
| JP | 2004-163312 A | 6/2004 | |
| JP | 2004-251814 A | 9/2004 | |
| JP | 2006-226698 A | 8/2006 | |
| JP | 2007-127415 A | 5/2007 | |
| JP | 2007-240424 A | 9/2007 | |

* cited by examiner

*Primary Examiner* — Abdullahi Nur
(74) *Attorney, Agent, or Firm* — Global IP Counselors, LLP (57) ABSTRACT

A fluorescence detecting device receives fluorescence emitted by n kinds of measurement objects within wavelength bands $FL_k$ (k is an integer of 1 to n) set so that the fluorescence intensity of fluorescence emitted by a measurement object k becomes higher than that of fluorescence emitted by the other one or more measurement objects, and acquires fluorescent signals corresponding to the wavelength bands $FL_k$ (k is an integer of 1 to n). Each of the fluorescent signals is subjected to frequency-down conversion by mixing it with a modulation signal for modulating the intensity of a laser beam $L_k$ (k=1) corresponding to at least one of the wavelength bands $FL_k$ to produce fluorescence data including the phase delay and intensity amplitude of the fluorescent signal. The fluorescence data is corrected to calculate the phase delay and a fluorescence relaxation time is calculated using the phase delay.

15 Claims, 6 Drawing Sheets

FLUORESCENCE DETECTING DEVICE AND FLUORESCENCE DETECTING METHOD

TECHNICAL FIELD

The present invention relates to a device and a method for detecting fluorescence by receiving fluorescence emitted by a measurement object, which is an analyte labeled with a fluorochrome, irradiated with laser light and then processing a fluorescent signal of the fluorescence.

BACKGROUND ART

In the medical and biological fields, flow cytometers are widely used. A flow cytometer analyzes the type, frequency, and characteristics of a measurement object such as cells or genes by allowing a photoelectric converter such as a photomultiplier or an avalanche photodiode to receive fluorescence emitted by the measurement object irradiated with laser light.

More specifically, in a flow cytometer, a suspension liquid containing a measurement object obtained by labeling an analyte such as a biological material (e.g., cells, DNA, RNA, enzymes, or proteins) with a fluorescent reagent is allowed to flow through a tube together with a sheath liquid flowing under pressure at a speed of about 10 m/s or less so that a laminar sheath flow is formed. The flow cytometer receives fluorescence emitted by a fluorochrome attached to the measurement object by irradiating the measurement object in the laminar sheath flow with laser light and identifies the analyte by using the fluorescence as a label.

Such a flow cytometer can measure the relative amounts of, for example, DNA, RNA, enzymes, proteins etc. contained in a cell, and also can quickly analyze their properties. Further, a cell sorter or the like is used to identify a specific type of cell or chromosome based on fluorescence and selectively and quickly collect only the identified specific cells or chromosomes alive.

When using such a cell sorter, the flow cytometer is required to quickly identify more kinds of measurement objects with high accuracy based on information about fluorescence.

Patent Document 1 discloses a fluorescence detecting device and a fluorescence detecting method which are capable of quickly identifying many kinds of measurement objects with high accuracy by calculating the fluorescence life (fluorescence relaxation time) of fluorescence emitted by a measurement object irradiated with laser light.

Patent Document 1 describes that the phase delay of a fluorescent signal of fluorescence emitted by a measurement object irradiated with intensity-modulated laser light with respect to a modulation signal used to modulate the intensity of the laser light is determined and the fluorescence relaxation time of the fluorescence is calculated from the phase delay.

However, the device and the method disclosed in Patent Document 1 have the following problem in effectively identifying two or more types of fluorescence emitted by measurement objects.

In order to measure measurement objects that emit two or more types of fluorescence, filters or the like corresponding to the wavelengths of respective fluorescence are used so that different photoelectric converters correspond to different wavelength bands. However, each fluorescence emitted by excitation with laser light has a broad wavelength spectrum, and is therefore received by two or more of the photoelectric converters. That is, a fluorescent signal generated by one photoelectric converter is not always a signal derived just from single fluorescence and may be a signal derived from a mixture of two or more types of fluorescence.

Therefore, when a phase delay is determined using such a fluorescent signal derived from a mixture of two or more types of fluorescence, an accurate fluorescence relaxation time cannot be obtained from such a phase delay.

PRIOR ART DOCUMENT

Patent Document

Patent Document 1: Japanese Patent Application Laid-Open No. 2006-226698

DISCLOSURE OF THE INVENTION

Problems to be Solved by the Invention

In order to solve the above problem, it is an object of the present invention to provide a fluorescence detecting device and a fluorescence detecting method which can achieve highly accurate calculation of a fluorescence relaxation time by receiving fluorescence emitted from n (n is an integer of 2 or more) kinds of measurement objects irradiated with laser light and then processing fluorescent signals of the received fluorescence.

Means for Solving the Problems

One aspect of the present invention provides a device for detecting fluorescence by receiving fluorescence emitted by n (n is an integer of 2 or more) kinds of measurement objects irradiated with laser light and processing fluorescent signals of the received fluorescence, the device including:

(A) a light source unit operable to modulate, at two or more different frequencies, intensities of laser beams $L_k$ (k is an integer of 1 to n) of different wavelengths prepared so as to correspond to measurement objects k so that optical absorption characteristics of each of the measurement objects are different from those of other one or more kinds of the measurement objects, and operable to output these laser beams $L_k$ as one irradiation light to irradiate the n kinds of measurement objects with the irradiation light;

(B) a light-receiving unit that includes two or more light-receiving elements operable to receive fluorescence emitted by the n kinds of measurement objects irradiated with the irradiation light within wavelength bands $FL_k$ (k is an integer of 1 to n) set so as to correspond to the measurement objects k (k is an integer of 1 to n) so that fluorescence intensity of fluorescence emitted by each of the measurement objects is different from that or those of fluorescence emitted by other one or more kinds of the measurement objects, and operable to output fluorescent signals corresponding to the wavelength bands $FL_k$;

(C) a first processing unit operable to perform frequency-down conversion by mixing each of the outputted fluorescent signals with a modulation signal for modulating at least one of the intensities of the laser beams $L_k$ corresponding to the wavelength bands $FL_k$ (k is an integer of 1 to n) as a first reference signal to produce fluorescence data containing a phase delay and an intensity amplitude of each of the fluorescent signals; and (D) a second processing unit operable to correct the produced fluorescence data and determine a phase delay of each of the fluorescent signals using the corrected fluorescence data, and to calculate a fluorescence relaxation time using the phase delay.

Another aspect of the present invention provides a method for detecting fluorescence by receiving fluorescence emitted by n (n is an integer of 2 or more) kinds of measurement objects irradiated with laser light and processing fluorescent signals of the received fluorescence, the method including:

(E) the first step of modulating, at two or more different frequencies, intensities of laser beams $L_k$ (k is an integer of 1 to n) of different wavelengths prepared so as to correspond to measurement objects k so that optical absorption characteristics of each of the measurement objects k (k is an integer of 1 to n) are different from those of other one or more kinds of the measurement objects and outputting these laser beams $L_k$ as one irradiation light to irradiate the n kinds of the measurement objects with the irradiation light;

(F) the second step of receiving fluorescence emitted by the n kinds of measurement objects irradiated with the irradiation light within wavelength bands $FL_k$ (k is an integer of 1 to n) set so as to correspond to the measurement objects k (k is an integer of 1 to n) so that fluorescence intensity of fluorescence emitted by each of the measurement objects k is different from that or those of fluorescence emitted by other one or more kinds of the measurement objects and outputting fluorescent signals corresponding to the wavelength bands $FL_k$;

(G) the third step of performing frequency-down conversion by mixing each of the outputted fluorescent signals with a modulation signal for modulating at a least one of intensities of the laser beams $L_k$ corresponding to the wavelength bands $FL_k$ (k is an integer of 1 to n) as a first reference signal, to produce fluorescence data containing a phase delay and an intensity amplitude of each of the fluorescent signals; and (H) the fourth step of correcting the produced fluorescence data, determining a phase delay of each of the fluorescent signals using the corrected fluorescence data, and calculating a fluorescence relaxation time using the phase delay.

Effects of the Invention

According to the above aspects of the present invention, fluorescence data containing the phase delay and the intensity amplitude of a fluorescent signal is corrected, the phase delay of the fluorescent signal is determined using the corrected fluorescence data, and a fluorescence relaxation time is calculated using the phase delay, which makes it possible to correct a fluorescence intensity and a fluorescence relaxation time at the same time and to remove adverse effects caused by received fluorescence other than fluorescence that should be measured. Thus, a fluorescence relaxation time can be calculated with a shot time and high accuracy.

Particularly, a plot of each of the fluorescent signals is represented in a scatter diagram having a vertical axis representing a fluorescence intensity in one of the two wavelength bands and a horizontal axis representing a fluorescence intensity in the other wavelength band, and then whether each fluorescence data is selected as an object to be corrected or not is determined based on the position of a plotting point of each fluorescent signals, which makes correction more accurate.

EMBODIMENT TO CARRY OUT THE INVENTION

Hereinbelow, the present invention will be described in detail based on a flow cytometer appropriately employing a fluorescence detecting device according to the present invention.

Figure 1:
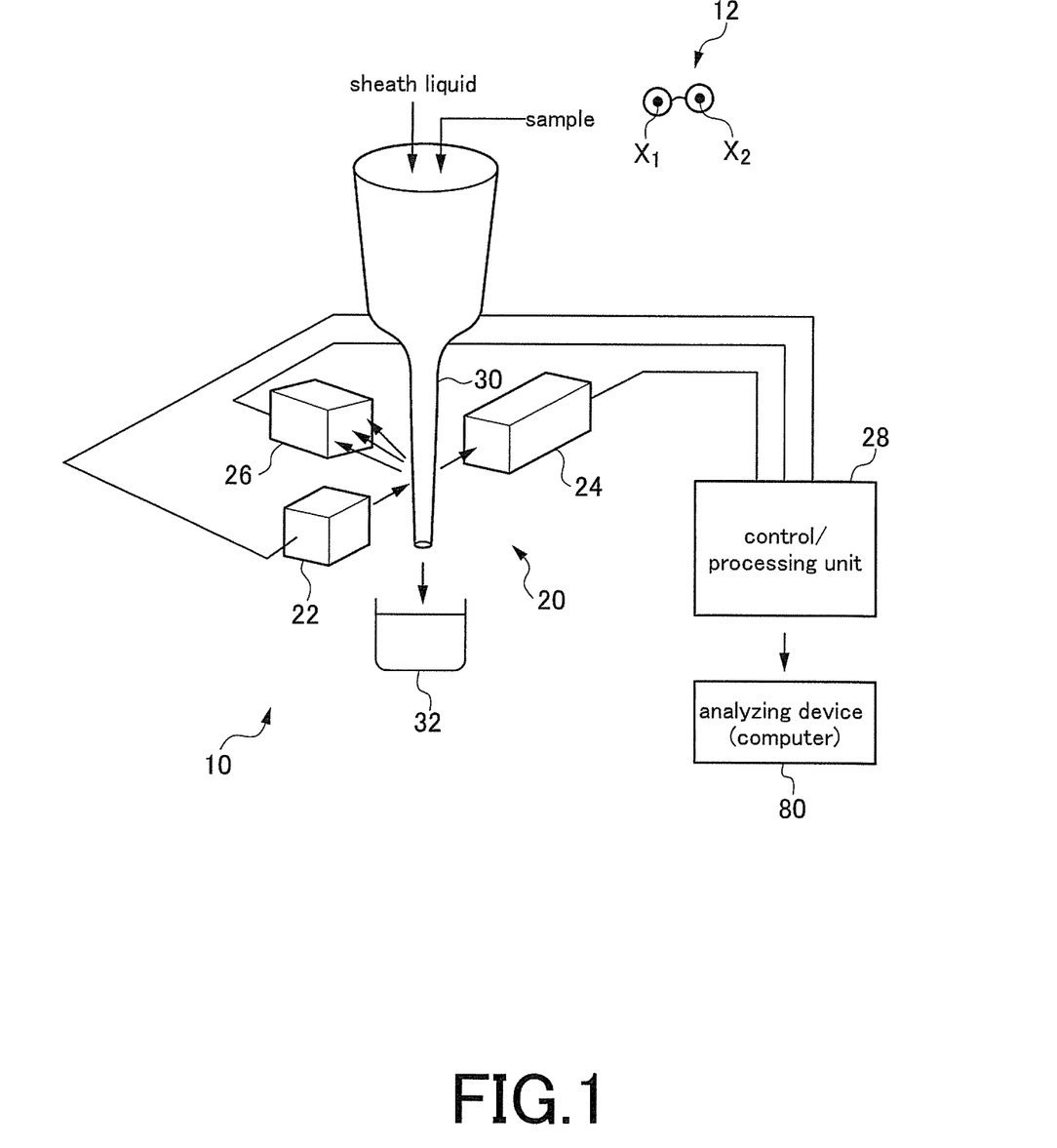
FIG. 1 is a schematic diagram illustrating the structure of a flow cytometer that uses a fluorescence detecting device according to the present invention using intensity-modulated laser light.

FIG. 1 is a schematic diagram illustrating the structure of a flow cytometer 10 that employs a fluorescence detecting device according to one embodiment of the present invention using intensity-modulated laser light.

The flow cytometer 10 includes a signal processing device 20 and an analyzing device (computer) 80. The signal processing device 20 detects and processes a fluorescent signal of fluorescence emitted by a sample 12, which is a measurement object, by irradiation with laser light. The analyzing device (computer) 80 calculates a fluorescence intensity and a fluorescence relaxation time from processing results obtained by the signal processing device 20. The following description is made with reference to a case where the sample 12 is composed of biologically-bound two cells (particles to be measured) that are close to each other to such an extent that FRET (Fluorescence Resonance Energy Transfer) is caused by a fluorescent protein (molecule) introduced into one of the cells and another fluorescent protein (molecule) introduced into the other cell. FRET is a phenomenon in which the energy of a first molecule is transferred to a second molecule without light emission. More specifically, the sample 12 is composed of biologically-bound two cells, into one of which a fluorescent protein $X_1$ has been introduced and into the other of which a fluorescent protein $X_2$ has been introduced.

The signal processing device 20 includes a laser light source unit 22, light-receiving units 24 and 26, a control/processing unit 28, and a tube 30.

The control/processing unit 28 includes a control unit that modulates the intensity of laser light emitted from the laser light source unit 22 at a predetermined frequency and a signal processing unit that processes a fluorescent signal from the sample 12.

The tube 30 allows an amount of samples 12 to flow individually therethrough together with a sheath liquid forming a high-speed flow so that a laminar sheath flow is formed. A collection vessel 32 is provided at the outlet of the tube 30. The flow cytometer 10 may include a cell sorter for quickly separating biological materials, such as specific cells, among the samples 12 after irradiation with laser light, thereby collecting the biological materials in another collection vessel.

The laser light source unit 22 is a unit that emits two laser beams different in wavelength, for example, a laser beam of $\lambda_1=408$ nm and a laser beam of $\lambda_2=473$ nm. A lens system is provided so that the laser beams are focused on a predetermined position in the tube 30, and the focus position is defined as a measurement point at which the sample 12 is measured.

Figure 2:
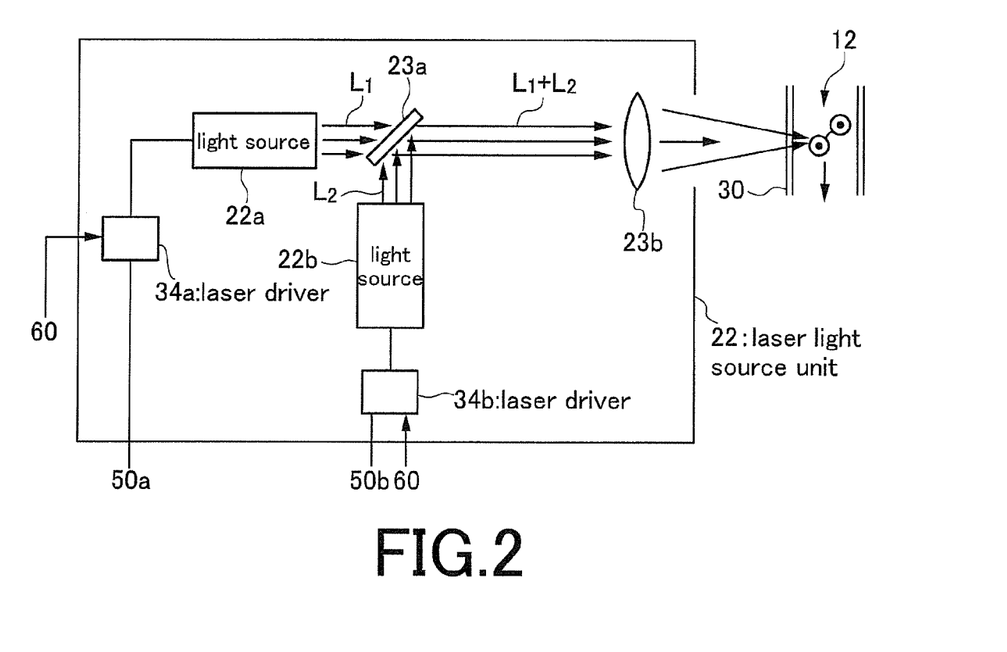
FIG. 2 is a schematic diagram illustrating the structure of one example of a light source unit used in the flow cytometer illustrated in FIG. 1.

FIG. 2 is a diagram illustrating one example of the structure of the laser light source unit 22.

The laser light source unit 22 emits intensity-modulated laser beams of wavelengths within a visible light range. The laser light source unit 22 includes a laser diode as a light source 22a and another laser diode as a light source 22b. The light source 22a emits a laser beam $L_1$ having a wavelength of 408 nm as a CW (continuous-wave) laser beam while modulating the intensity of the CW laser beam $L_1$ at a predetermined frequency. The light source 22b emits a laser beam $L_2$ having a wavelength of 473 nm as a CW laser beam while modulating the intensity of the CW laser beam at a predetermined frequency. The laser light source unit 22 further includes a dichroic mirror 23a, a lens system 23b, and laser drivers 34a and 34b.

The dichroic mirror 23a transmits laser light of wavelengths within a specific wavelength band and reflects laser light of wavelengths outside the specific wavelength band. The lens system 23b focuses laser light $L_1+L_2$ composed of the laser beam $L_1$ and the laser beam $L_2$ on the measurement point in the tube 30. The laser driver 34a drives the light source 22a and the laser driver 34b drives the light source 22b.

As the light sources that emit laser beams, for example, semiconductor lasers are employed.

Each of the laser beams have an output of, for example, about 5 to 100 mW. The laser beams are prepared so as to correspond to the fluorescent proteins $X_1$ and $X_2$ respectively so that the optical absorption characteristics (optical absorptance) of one of the fluorescent proteins become higher than those (that) of the other fluorescent protein. It is to be noted that in this embodiment, the wavelengths of the laser beams are set so that the optical absorption (optical absorptance) of one of the fluorescent proteins becomes higher than that of the other fluorescent protein, but may be set so that the optical absorption (optical absorptance) of one of the fluorescent proteins is different from that of the other fluorescent protein.

A frequency (modulation frequency) used to modulate the intensity of each of the laser beams $L_1$ and $L_2$ has a periodic time slightly longer than a fluorescence relaxation time, and is, for example, 10 to 50 MHz. A frequency used to modulate the intensity of the laser beam $L_1$ and a frequency used to modulate the intensity of the laser beam $L_2$ are different from each other, thereby allowing the sample 12 excited by the laser beams to emit fluorescence of different frequencies, so as to identify which of the laser beams has induced the emission of received fluorescence and separate information about fluorescence.

The dichroic mirror 23a is a mirror that transmits the laser beam $L_1$ and reflects the laser beam $L_2$. The laser beam $L_1$ and the laser beam $L_2$ are combined into one irradiation light by the dichroic mirror 23a, and the sample 12 is irradiated with the irradiation light at the measurement point.

The light sources 22a and 22b oscillate at predetermined wavelength bands so that fluorochromes are excited by the laser beams $L_1$ and $L_2$ and emit fluorescence of specific wavelength bands. The fluorescent proteins $X_1$ and $X_2$ to be excited by the laser beams $L_1$ and $L_2$ are introduced into and attached to the inside of two cells, respectively, and the sample 12 is composed of the two cells biologically bound together. When passing through the measurement point in the tube 30, the sample 12 is irradiated with the laser beams $L_1$ and $L_2$ at the measurement point, and then the fluorescent proteins $X_1$ and $X_2$ emit fluorescence at specific wavelengths.

The light-receiving unit 24 is arranged so as to be opposed to the laser light source unit 22 with the tube 30 being provided therebetween. The light-receiving unit 24 is equipped with a photoelectric converter that detects forward scattering of laser light caused by the sample 12 passing through the measurement point and outputs a detection signal indicating the passage of the sample 12 through the measurement point. The detection signal outputted from the light-receiving unit 24 is supplied to the analyzing device 80 and is used as a trigger signal to announce the timing of passage of the sample 12 through the measurement point in the tube 30 and as an ON signal for controlling the start of processing or an OFF signal.

On the other hand, the light-receiving unit 26 is arranged in a direction perpendicular to a direction in which laser light emitted from the laser light source unit 22 travels and to a direction in which the samples 12 move in the tube 30. The light-receiving unit 26 is equipped with two or more photoelectric converters that receive fluorescence emitted by the sample 12 irradiated with laser light at the measurement point.

Figure 3:
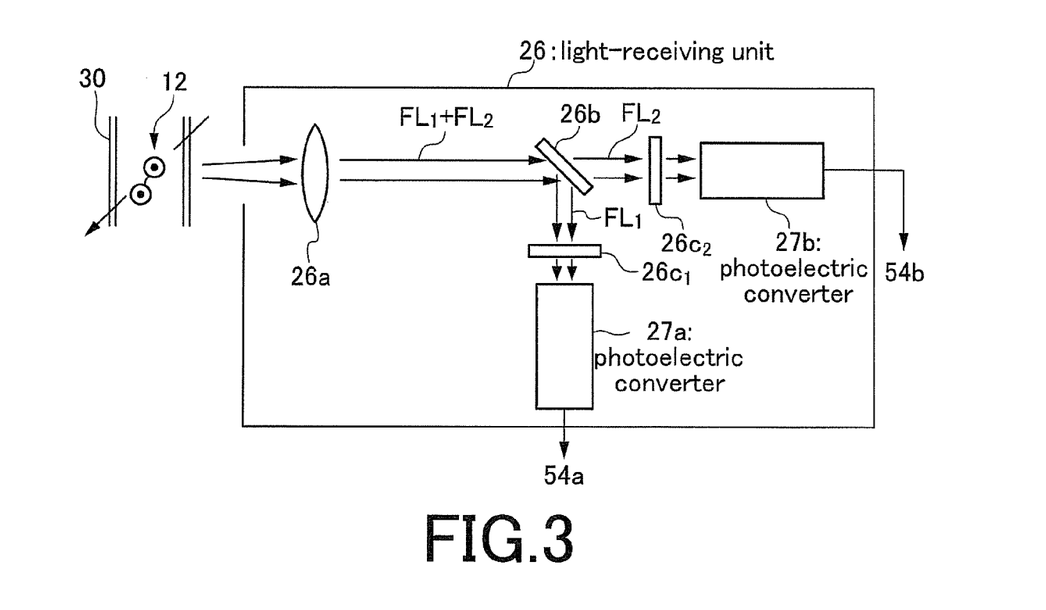
FIG. 3 is a schematic diagram illustrating the structure of one example of a light-receiving unit used in the flow cytometer illustrated in FIG. 1.

FIG. 3 is a schematic diagram illustrating the structure of one example of the light-receiving unit 26.

The light-receiving unit 26 illustrated in FIG. 3 includes a lens system 26a that focuses fluorescent signals from the sample 12, a dichroic mirror 26b, band-pass filters $26c_1$ and $26c_2$, and photoelectric converters (light-receiving elements) 27a and 27b such as photomultipliers.

The lens system 26a focuses fluorescence received by the light-receiving unit 26 on the light-receiving surfaces of the photoelectric converters 27a and 27b.

The dichroic mirror 26b is a mirror that reflects fluorescence of wavelengths within a predetermined wavelength band but transmits fluorescence of wavelengths outside the predetermined wavelength band. The reflection wavelength band of the dichroic mirror 26b and the transmission wavelength bands of the band-pass filters $26c_1$ and $26c_2$ are set so that fluorescence of a predetermined wavelength band can be received by the photoelectric converter 27a after filtering by the band-pass filter $26c_1$ and fluorescence of a predetermined wavelength band can be received by the photoelectric converter 27b after filtering by the band-pass filter $26c_2$.

The band-pass filter $26c_1$ is provided in front of the light-receiving surface of the photoelectric converter 27a and transmits only fluorescence of a predetermined wavelength band, and the band-pass filter $26c_2$ is provided in front of the light-receiving surface of the photoelectric converter 27b and transmits only fluorescence of a predetermined wavelength band. The wavelength bands of fluorescence that can pass through the band-pass filters $26c_1$ and $26c_2$ are set so as to correspond to the wavelength bands of fluorescence emitted by the fluorescent proteins $X_1$ and $X_2$. For example, the transmission wavelength band of the band-pass filter $26c_1$ is set to a wavelength band $FL_1$ ranging from 494 to 535 nm to mainly receive fluorescence emitted by irradiation with the laser beam $L_1$ of 408 nm emitted from the light source 22a, and the transmission wavelength band of the band-pass filter $26c_2$ is set to a wavelength band $FL_2$ ranging from 540 to 570 nm to mainly receive fluorescence emitted by irradiation with the laser beam $L_2$ of 473 nm emitted from the light source 22b.

The wavelength band $FL_1$ is set so as to correspond to fluorescence emitted by the fluorescent protein $X_1$ so that the fluorescence intensity of fluorescence emitted by the fluorescent protein $X_1$ of the sample 12 irradiated with the laser beam $L_1$ becomes higher than that of fluorescence emitted by the fluorescent protein $X_2$ of the sample 12 irradiated with the laser beam $L_1$. Similarly, the wavelength band $FL_2$ is set so as to correspond to fluorescence emitted by the fluorescent protein $X_2$ so that the fluorescence intensity of fluorescence emitted by the fluorescent protein $X_2$ of the sample 12 irradiated with the laser beam $L_2$ becomes higher than that of fluorescence emitted by the fluorescent protein $X_1$ of the sample 12 irradiated with the laser beam $L_2$.

It is to be noted that, in this embodiment, the wavelength band $FL_1$ may be set so as to correspond to the fluorescent protein $X_1$ so that the fluorescence intensity of fluorescence emitted by the fluorescent protein $X_1$ is different from that of fluorescence emitted by the fluorescent protein $X_2$ and the wavelength band $FL_2$ may be set so as to correspond to the fluorescent protein $X_2$ so that the fluorescence intensity of fluorescence emitted by the fluorescent protein $X_2$ is different from that of fluorescence emitted by the fluorescent protein $X_1$.

The photoelectric converters 27a and 27b are each a light-receiving element equipped with, for example, a photomultiplier as a sensor to convert light received by its photoelectric surface into an electric signal. Here, the emission of fluorescence to be received by each of the photoelectric converters is induced by excitation with laser light whose intensity is modulated at a predetermined frequency, and therefore a fluorescent signal outputted from each of the photoelectric converters is a signal whose intensity varies at a predetermined frequency. The fluorescent signal is supplied to the control/processing unit 28.

Figure 4:
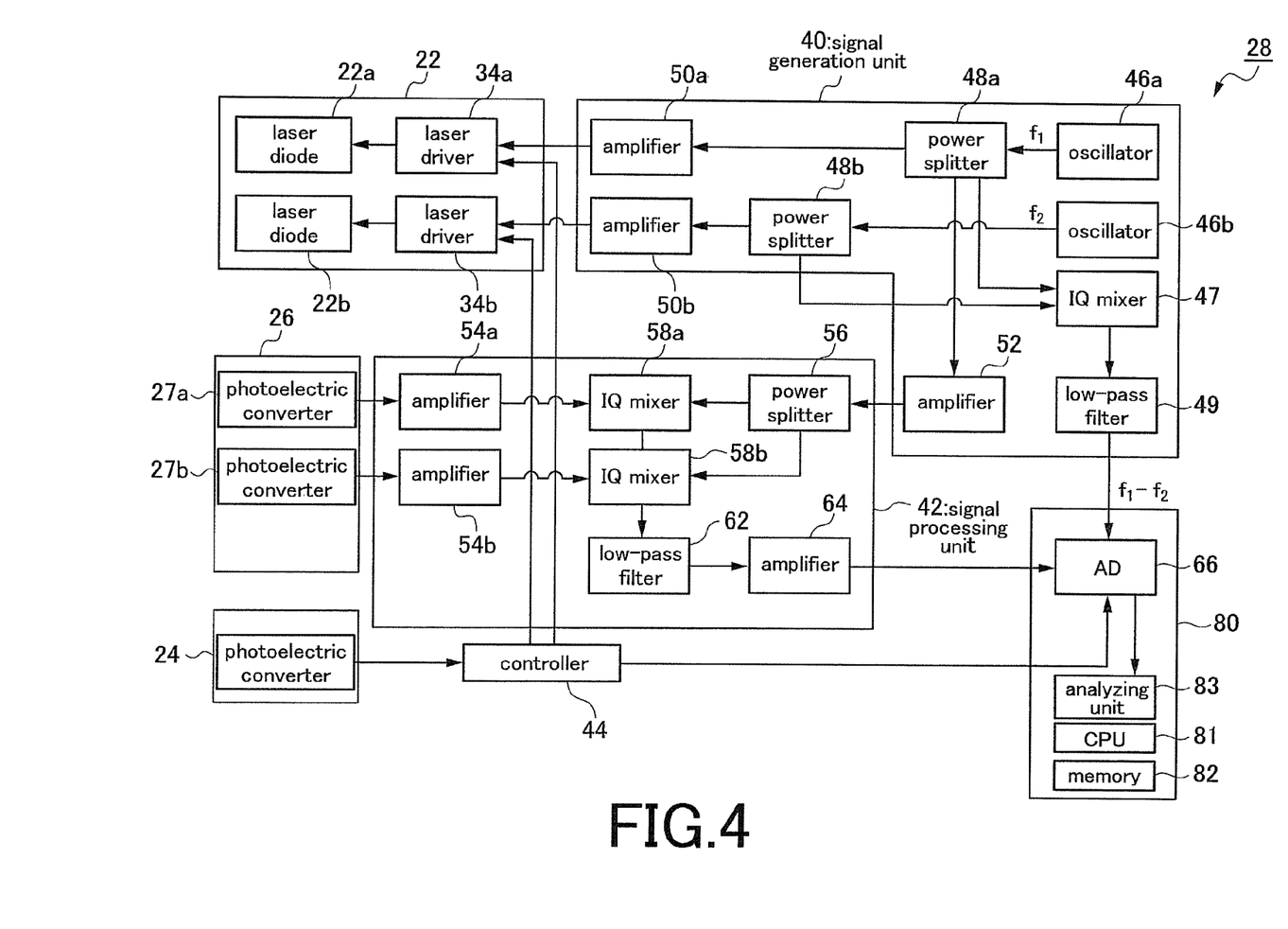
FIG. 4 is a schematic structural diagram of the flow cytometer illustrated in FIG. 1, which mainly illustrates one example of a control/processing unit used in the flow cytometer.

As illustrated in FIG. 4, the control/processing unit 28 includes a signal generation unit 40, a signal processing unit 42, and a controller 44 as a control unit.

The signal generation unit 40 is a unit that generates a modulation signal for modulating the intensity of the laser beam $L_1$ at a predetermined frequency and a modulation signal for modulating the intensity of the laser beam $L_2$ at a predetermined frequency.

More specifically, the signal generation unit 40 includes oscillators 46a and 46b, power splitters 48a and 48b, amplifiers 50a, 50b, and 52, an IQ mixer 47, and a low-pass filter 49. The signal generation unit 40 supplies a modulation signal with a frequency of $f_1$ generated by the oscillator 46a and amplified by the amplifier 50a and a modulation signal with a frequency of $f_2$ ($f_2 > f_1$) generated by the oscillator 46b and amplified by the amplifier 50b to the laser drivers 34a and 34b of the laser light source unit 22, respectively, and also supplies a modulation signal with a frequency of $f_1$ amplified by the amplifier 52 to the signal processing unit 42. As will be described later, the modulation signal with a frequency of $f_1$ supplied to the signal processing unit 42 is used as a first reference signal for detecting fluorescent signals outputted from the photoelectric converters 27a and 27b. It is to be noted that the modulation signals are each a sinusoidal signal with a predetermined frequency, and the frequency is set to a value in the range of 10 to 50 MHz. The oscillator 46a generates a signal with a frequency of $f_1$ and the oscillator 46b generates a signal with a frequency of $f_2$ different from $f_1$ so that modulation signals different in frequency are generated.

The modulation signal with a frequency of $f_1$ split by the power splitter 48a and the modulation signal with a frequency of $f_2$ split by the power splitter 48b are supplied to the IQ mixer 47 and then filtered through the low-pass filter 49 to extract a low-frequency component. As a result, a differential signal of the modulation signal with a frequency of $f_2$ with respect to the modulation signal with a frequency of $f_1$ is generated. This differential signal has a frequency equal to a differential frequency of $(f_2-f_1)$. The differential signal is supplied to the analyzing device 80 and is used as a second reference signal in an analyzing unit 83 (which will be described later) for frequency-down conversion.

The signal processing unit 42 is a unit that extracts, by using fluorescent signals outputted from the photoelectric converters 27a and 27b, information about the phase delay of fluorescence emitted by the two fluorescent proteins irradiated with laser light. The signal processing unit 42 includes amplifiers 54a and 54b, IQ mixers 58a and 58b, a low-pass filter 62, and an amplifier 64.

The amplifier 54a amplifies a fluorescent signal outputted from the photoelectric converter 27a and the amplifier 54b amplifies a fluorescent signal outputted from the photoelectric converter 27b. Each of the IQ mixers 58a and 58b mixes the amplified fluorescent signal with the modulation signal (first reference signal) that is a sinusoidal signal supplied from the signal generation unit 40.

As described above, the IQ mixer 58a mixes the fluorescent signal supplied from the photoelectric converter 27a with the modulation signal supplied from the signal generation unit 40, and the IQ mixer 58b mixes the fluorescent signal supplied from the photoelectric converter 27b with the modulation signal supplied from the signal generation unit 40. More specifically, each of the IQ mixers 58a and 58b multiplies the first reference signal by the fluorescent signal (RF signal) to generate a signal containing an in-phase component of the fluorescent signal with the modulation signal and a signal containing a 90 degrees-phase shifted component of the fluorescent signal with respect to the modulation signal. The signal containing an in-phase component is generated by mixing the modulation signal with the fluorescent signal, and the signal containing a 90 degrees-phase shifted component is generated by mixing a signal obtained by shifting the phase of the modulation signal by 90° with the fluorescent signal.

The low-pass filter 62 is a unit that filters signals generated by the IQ mixers 58a and 58b to extract low-frequency components. By performing the filtering, a component (Re component) of the fluorescent signal in-phase with the first reference signal with a frequency of $f_1$ and a component (Im component) of the fluorescent signal phase-shifted by 90 degrees with respect to the first reference signal with a frequency of $f_1$ are extracted as fluorescence data, and the fluorescence data is amplified by the amplifier 64 with a predetermined gain and sent to an A/D converter 66. The extracted fluorescence data mainly includes a DC component and a signal component with a frequency of $(f_2-f_1)$.

The Re component and the Im component can be obtained from both the wavelength band $FL_1$ corresponding to the photoelectric converter 27a and the wavelength band $FL_2$ corresponding to the photoelectric converter 27b. Therefore, a pair of the Re component and the Im component obtained from the wavelength band $FL_1$ and a pair of the Re component and the Im component obtained from the wavelength band $FL_2$ are sent to the A/D converter 66. Each of the Re component and the Im component includes a DC component and a signal component with a frequency of $(f_2-f_1)$.

The controller 44 controls the signal generation unit 40 to generate modulation signals with predetermined frequencies, and further gives instructions for starting and stopping A/D conversion performed in the analyzing device 80.

More specifically, the controller 44 gives instructions for controlling the operations of the individual units and manages all the operations of the flow cytometer 10. Further, the controller 44 gives instructions for starting and stopping the A/D converter 66 that samples the Re component and the Im component generated by the signal processing unit 42. The controller 44 uses a light-receiving signal outputted by the light-receiving unit 24 as an ON/OFF signal for controlling the start and stop of A/D conversion to direct the A/D converter 66 to start and stop A/D conversion. Further, the controller 44 determines the oscillating frequencies of the oscillators 46a and 46b to modulate the intensities of the laser beams.

The analyzing device 80 includes the A/D converter 66 and the analyzing unit 83 that determines, from the A/D-converted Re component and the A/D-converted Im component, the phase delay angle of fluorescence with respect to the laser beam and further determines, from the phase delay angle, a fluorescence relaxation time constant (fluorescence relaxation time) and a fluorescence intensity.

The A/D converter 66 converts the Re component and the Im component supplied from the signal processing unit 42 into digital data, and also converts the differential signal supplied from the signal generation unit 40 into digital data. The digital data is supplied to the analyzing unit 83.

Figure 5:
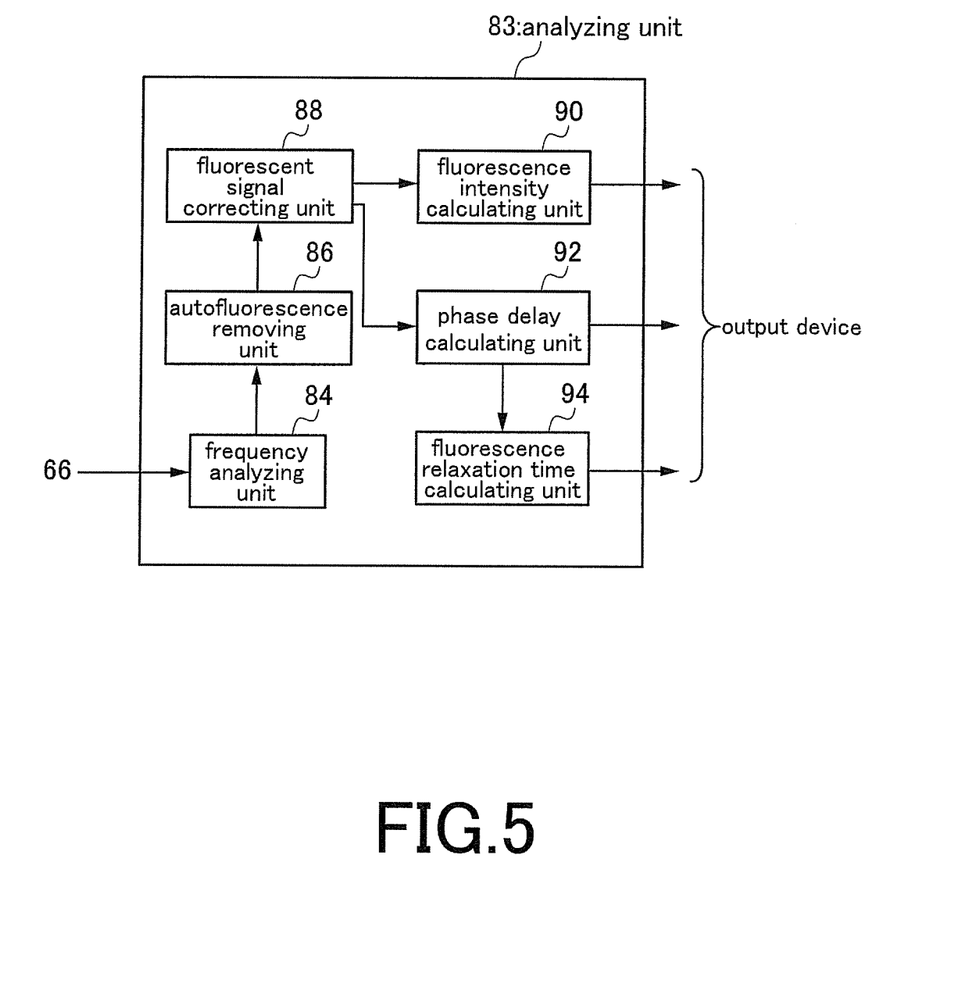
FIG. 5 is a schematic diagram illustrating the structure of one example of an analyzing device used in the flow cytometer illustrated in FIG. 1.

FIG. 5 is a schematic diagram illustrating the structure of the analyzing unit 83 of the analyzing device 80.

The analyzing unit 83 includes a frequency analyzing unit 84, an autofluorescence removing unit 86, a fluorescence data correcting unit 88, a fluorescence intensity calculating unit 90, a phase delay calculating unit 92, and a fluorescence relaxation time calculating unit 94. These units are software modules performing their functions by executing software on the computer including a CPU 81 and a memory 82. However, these units can be, of course, provided by dedicated circuits.

The frequency analyzing unit 84 is a unit that divides each of the Re component and the Im component supplied from the signal processing unit 42 and then subjected to A/D conversion into a DC component and a signal component with a differential frequency of $(f_2-f_1)$. The frequency analyzing unit 84 and the signal processing unit 42 constitute a first processing unit that performs frequency-down conversion in the present invention.

The frequency analyzing unit 84 determines the DC component of the Re component and the DC component of the Im component by performing FFT (Fast Fourier Transformation) processing on the signal of the Re component and the signal of the Im component, which are supplied from the signal processing unit 42 and then subjected to A/D conversion. Thereby fluorescence data (Re component, Im component) containing the phase delay and intensity amplitude of the fluorescent signal at a frequency of $f_1$ is extracted. Further, the frequency analyzing unit 84 performs frequency-down conversion on the signal of the Re component and the signal of the Im component, which are supplied from the signal processing unit 42 and then subjected to A/D conversion by using, as a second reference signal, the differential signal with a frequency of $(f_2-f_1)$ supplied from the signal generation unit 40. Thereby fluorescence data (Re component, Im component) containing the phase delay and intensity amplitude of the fluorescent signal at a frequency of $f_2$ is extracted.

The Re component and the Im component supplied from the signal processing unit 42 are signals obtained by performing frequency-down conversion on the fluorescent signal by using a frequency of $f_1$, and therefore the DC component contains the phase delay of the fluorescent signal at a frequency of $f_1$ with respect to the modulation signal with a frequency of $f_1$ and the intensity amplitude of the fluorescent signal at a frequency of $f_1$. On the other hand, the signal component with a frequency of $(f_2-f_1)$ contains the phase delay of the fluorescent signal at a frequency of $f_2$ with respect to the modulation signal with a frequency of $f_2$ and the intensity amplitude of the fluorescent signal at a frequency of $f_2$.

Therefore, the frequency analyzing unit 84 obtains fluorescence data, which contains the phase delay and intensity amplitude of fluorescence emitted by irradiation with the laser beam $L_1$ whose intensity is modulated at a frequency of $f_1$, by extracting the DC components by FFT processing. Further, the frequency analyzing unit 84 obtains fluorescence data, which contains the phase delay and intensity amplitude of fluorescence emitted by irradiation with the laser beam $L_2$ whose intensity is modulated at a frequency of $f_2$, by extracting the signal components with a frequency of $(f_2-f_1)$ by performing frequency-down conversion by software using the differential signal with a frequency of $(f_2-f_1)$ as a second reference signal. The thus obtained fluorescence data is supplied to the autofluorescence removing unit 86.

The autofluorescence removing unit 86 is a unit that determines whether received fluorescence is autofluorescence by using the supplied fluorescence data composed of the Re component and the Im component and removes the Re component and the Im component satisfying certain conditions as fluorescence data of autofluorescence so that the subsequent processing is not performed on the fluorescence data of autofluorescence. More specifically, a fluorescence intensity is determined using the Re component and the Im component of the fluorescent signal obtained from the wavelength band $FL_1$ and a fluorescence intensity is determined using the Re component and the Im component of the fluorescent signal obtained from the wavelength band $FL_2$, and a plot of these fluorescence intensities is represented on a two-dimensional coordinate system of a scatter diagram having a vertical axis representing a fluorescence intensity in one of the two wavelength bands and a horizontal axis representing a fluorescence intensity in the other wavelength band. When the plot point is not located within a predetermined range corresponding to autofluorescence, the Re component and the Im component of the fluorescence data are selected as objects to be processed, including correction processing. On the other hand, when the plotted point is located in the range corresponding to autofluorescence in the scatter diagram, the Re component and the Im component of the fluorescent data are removed from objects to be processed further, that is, are not selected as objects to be processed further.

Figure 6:
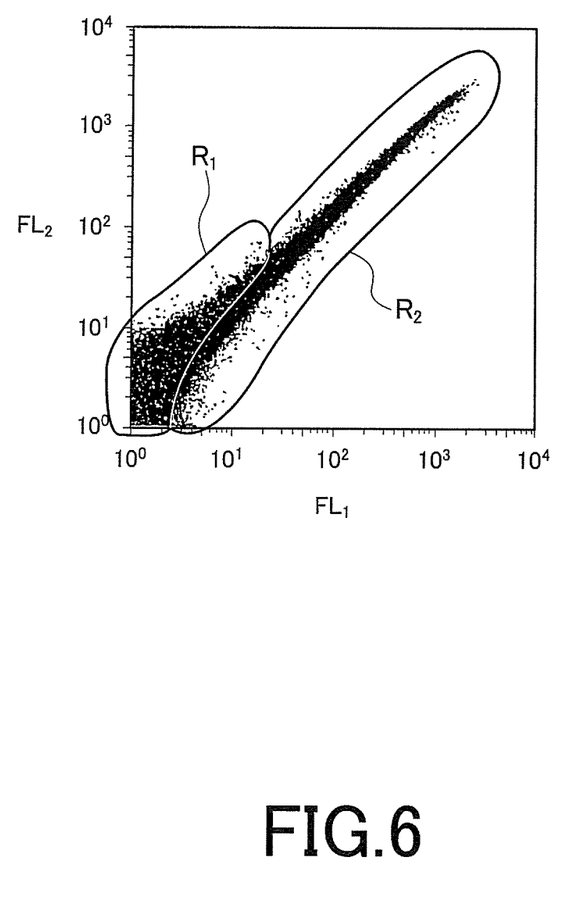
FIG. 6 is a graph indicating a range corresponding to autofluorescence measured the flow cytometer illustrated in FIG. 1.

Such a range corresponding to autofluorescence is determined by measuring the samples 12 (particles to be measured), such as cells, containing no fluorescent proteins therein by the flow cytometer 10 and representing, in a scatter diagram, a plot of fluorescence intensities determined using Re components and Im components outputted from the signal processing device 20.

The reason why the fluorescence data of autofluorescence is removed from objects to be processed further is that more accurate correction can be performed using the fluorescence data of fluorescence emitted by the fluorescent proteins.

FIG. 6 is a diagram illustrating one example of the scatter diagram. In the scatter diagram illustrated in FIG. 6, the horizontal axis represents a fluorescence intensity in the wavelength band $FL_1$ and the vertical axis represents a fluorescence intensity in the wavelength band $FL_2$. In this case, the predetermined range corresponding to autofluorescence is represented as $R_1$. Fluorescence data plotted in the range $R_1$ is determined as the fluorescence data of autofluorescence and is therefore removed. On the other hand, fluorescence data plotted in a range $R_2$ is subjected to the further processing.

The fluorescence data correcting unit 88 is a unit that corrects fluorescence data from which the fluorescence data of autofluorescence has been removed.

Figure 7A:
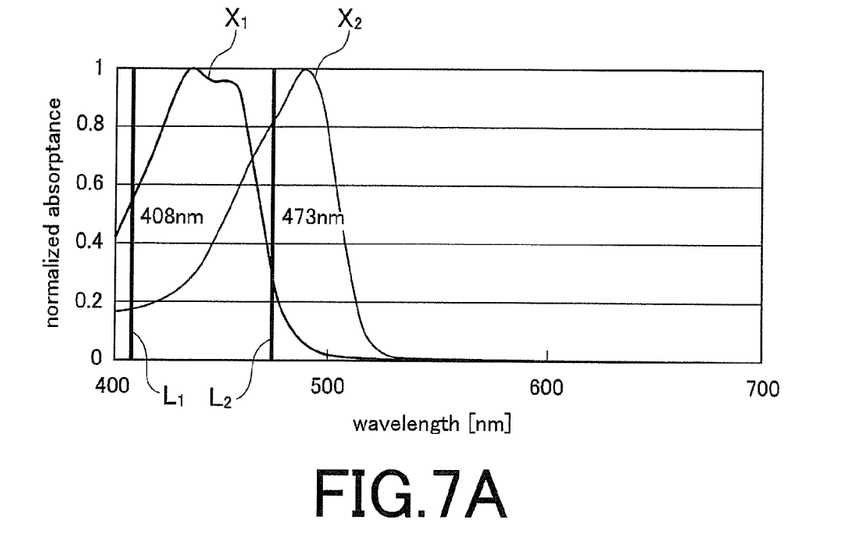
FIG. 7(a) is a graph illustrating the optical absorption characteristics of fluorescent proteins and FIG. 7(b) is a graph illustrating the fluorescence characteristics of the fluorescent proteins.

FIG. 7(a) is a graph illustrating the absorption characteristics of the fluorescent protein $X_1$ when the laser beam $L_1$ is used and the absorption characteristics of the fluorescent protein $X_2$ when the laser beam $L_2$ is used. As illustrated in FIG. 7(a), the absorption characteristics have a broad distribution. Therefore, irradiation with the laser beam $L_1$ induces optical absorption and excitation of not only the fluorescent protein $X_1$ but also the fluorescent protein $X_2$. Similarly, irradiation with the laser beam $L_2$ induces optical absorption and excitation of not only the fluorescent protein $X_2$ but also the fluorescent protein $X_1$.

Figure 7B:
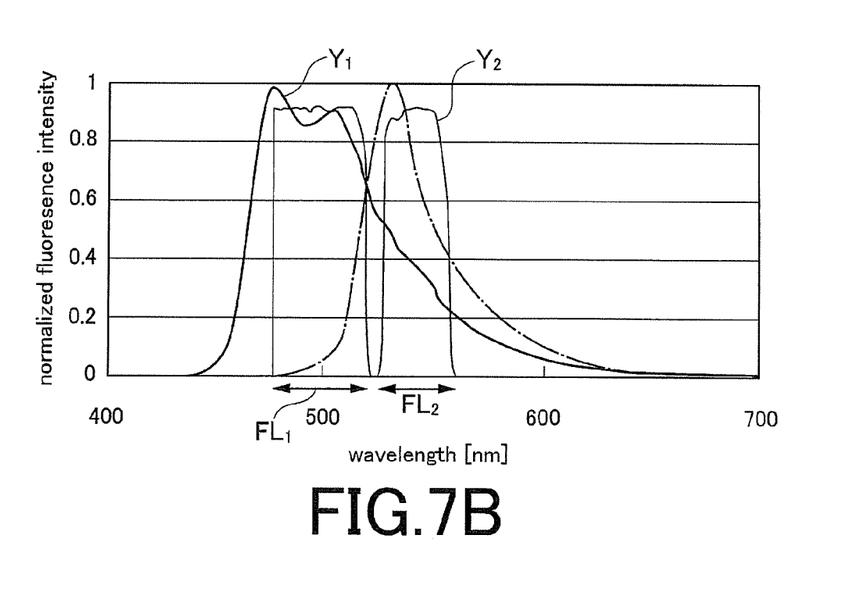

FIG. 7(b) is a graph illustrating the fluorescence characteristics of the excited fluorescent protein $X_1$ and the fluorescence characteristics of the excited fluorescent protein $X_2$. As illustrated in FIG. 7(b), part of fluorescence $Y_2$ emitted by the fluorescent protein $X_2$ by excitation with the laser beam $L_1$ is received within the wavelength band $FL_1$ set to mainly receive fluorescence $Y_1$ emitted by the fluorescent protein $X_1$. Similarly, part of fluorescence $Y_1$ emitted by the fluorescent protein $X_1$ by excitation with the laser beam $L_2$ is received within the wavelength band $FL_2$ set to mainly receive fluorescence $Y_2$ emitted by the fluorescent protein $X_2$.

Therefore, fluorescence data obtained by receiving fluorescence within the wavelength band $FL_1$ contains not only the fluorescence data of fluorescence $Y_1$ emitted by the fluorescent protein $X_1$ by excitation with the laser beam $L_1$ but also the fluorescence data of fluorescence $Y_2$ emitted by the fluorescent protein $X_2$ by excitation with the laser beam $L_1$. Similarly, fluorescence data obtained by receiving fluorescence within the wavelength band $FL_2$ contains not only the fluorescence data of fluorescence $Y_2$ emitted by the fluorescence protein $X_2$ by excitation with the laser beam $L_2$ but also the fluorescence data of fluorescence $Y_1$ emitted by the fluorescent protein $X_1$ by excitation with the laser beam $L_2$. The fluorescence data of fluorescence $Y_2$ whose wavelength is contained in the wavelength band $FL_1$ is obtained by excitation with the same laser beam and therefore cannot be separated using the difference between the two frequencies for modulating the intensities of the laser beams $L_1$ and $L_2$. The fluorescence data of fluorescence $Y_1$ whose wavelength is contained in the wavelength band $FL_2$ is obtained by excitation with the same laser beam and therefore cannot be separated using the difference between the two frequencies for modulating the intensities of the laser beams $L_1$ and $L_2$. For this reason, the fluorescence data correcting unit 88 corrects the fluorescence data.

The fluorescence data correcting unit 88 performs correction in the following manner. The fluorescence data correcting unit 88 stores, in advance, reference fluorescence data. The reference fluorescence data is obtained by measuring the fluorescent proteins $X_1$ and $X_2$ separately using the signal processing device 20 including the light source unit 22, the light-receiving units 24 and 26, and the control/processing unit 28 and contains a reference phase delay and a reference intensity amplitude. The fluorescence data correcting unit 88 corrects fluorescence data using a correction matrix composed of the reference fluorescence data.

More specifically, the reference fluorescence data is represented by $a_{km} \cdot e^{(-i\theta km)}$ ($a_{km}$ is a reference intensity amplitude of the fluorescent signal, $\theta_{km}$ is a reference phase delay of the fluorescent signal) as information, which is produced from a fluorescent signal of a fluorescent protein k (k is an integer of 1 to n) outputted by a photoelectric converter corresponding to a wavelength band $FL_m$ (m is an integer of 1 to n). Then, the fluorescence data corresponding to the wavelength band $FL_m$ is defined as $A_s'$ (s is an integer of 1 to n), and corrected fluorescence data is defined as $A_s$ (s=1 to n) ($A_s'$ and $A_s$ are each represented by a complex number, i.e., (Re component)+i(Im component)). The fluorescence data correcting unit 88 corrects the fluorescence data by calculating $A_s$ from $A_s'$ according to the following formula (1). Here, the fluorescence data $A_s'$ and the fluorescence data $A_s$ are each represented by a complex number containing information about a fluorescence intensity and a phase delay.

For example, fluorescence data $A_1'$ measured in a wavelength band $FL_1$ contains not only the fluorescence component of a fluorescent protein 1 but also the fluorescence components of fluorescent proteins 2 to n. The ratio of the fluorescence data of fluorescence emitted by the fluorescent proteins 2 to n contained in the fluorescence data $A_1'$ measured in the wavelength band $FL_1$ is represented as $a_{21}/a_{22} \cdot e^{-i(\theta 21-\theta 22)}$ to $a_{n1}/a_{n1}/a_{nn} \cdot e^{-i(\theta 21-\theta nn)}$. Therefore, the fluorescence data $A_1'$ measured in the wavelength band $FL_1$ is represented by the following formula using fluorescence data $A_1, A_2$ to $A_n$ to be determined and coefficients represented as $a_{21}/a_{22} \cdot e^{-i(\theta 21-\theta 22)}$ to $a_{n1}/a_{nn} \cdot e^{-i(\theta 21-\theta nn)}$: $A1'=A_1+a_{21}/a_{22} \cdot e^{-i(\theta 21-\theta 22)} \cdot A_2 + \ldots + a_{n1}/a_{nn} \cdot e^{-i(\theta 21-\theta nn)} \cdot A_n$ The following formula (1) represents $A_1'$ to $A_n'$ using the above formula. That is, fluorescence data $A_1$ to $A_n$ to be determined can be determined by correcting the fluorescence data $A_1'$ to $A_n'$ measured in the wavelength bands $FL_1$ to $FL_n$ with the individual elements of the inverse matrix of the right-hand side of the formula (1), that is, with the coefficients composed of the reference fluorescence data.

Formula (1)

$$\begin{Bmatrix} A_1 \\ A_2 \\ \vdots \\ A_n \end{Bmatrix} = \begin{bmatrix} 1 & \frac{a_{21}}{a_{22}}e^{-i(\theta_{21}-\theta_{22})} & \frac{a_{31}}{a_{33}}e^{-i(\theta_{31}-\theta_{33})} & \ldots \\ \frac{a_{12}}{a_{11}}e^{-i(\theta_{12}-\theta_{11})} & 1 & \frac{a_{32}}{a_{33}}e^{-i(\theta_{32}-\theta_{33})} & \ldots \\ \vdots & \vdots & \vdots & \\ \frac{a_{1n}}{a_{11}}e^{-i(\theta_{1n}-\theta_{11})} & \frac{a_{2n}}{a_{22}}e^{-i(\theta_{2n}-\theta_{22})} & \frac{a_{3n}}{a_{33}}e^{-i(\theta_{3n}-\theta_{33})} & \ldots \end{bmatrix}^{-1} \begin{Bmatrix} A_1' \\ A_2' \\ \vdots \\ A_n' \end{Bmatrix}$$

When fluorescence within the wavelength band $FL_1$ and fluorescence within the wavelength band $FL_2$ emitted from the fluorescent proteins $X_1$ and $X_2$ irradiated with the laser beams $L_1$ and $L_2$ are received, the following formulas (2) and (3) can be obtained.

In this way, the fluorescence data $A_1'$ measured in the wavelength band $FL_1$ is corrected, and the fluorescence data of fluorescence $Y_1$ emitted by the fluorescent protein $X_1$ is obtained as corrected fluorescence data $A_1$. Similarly, the fluorescence data $A_2'$ measured in the wavelength band $FL_2$ is corrected, and the fluorescence data of fluorescence $Y_2$ emitted by the fluorescent protein $X_2$ is obtained as corrected fluorescence data $A_2$. The corrected fluorescence data $A_1$ and the corrected fluorescence data $A_2$ are sent to the fluorescence intensity calculating unit 90 and the phase delay calculating unit 92.

Formula (2)

$$\begin{Bmatrix} A_1' \\ A_2' \end{Bmatrix} = \underbrace{\begin{bmatrix} 1 & \frac{a_{21}}{a_{22}}e^{-i(\theta_{21}-\theta_{22})} \\ \frac{a_{12}}{a_{11}}e^{-i(\theta_{12}-\theta_{11})} & 1 \end{bmatrix}}_{M} \begin{Bmatrix} A_1 \\ A_2 \end{Bmatrix} \quad (2)$$

-continued

Formula (3)

$$\begin{Bmatrix} A_1 \\ A_2 \end{Bmatrix} = [M]^{-1} \begin{Bmatrix} A'_1 \\ A'_2 \end{Bmatrix} \quad (3)$$

The fluorescence intensity calculating unit 90 is a unit that calculates a fluorescence intensity by determining the absolute value of a complex number representing the corrected fluorescence data $A_1$ and the absolute value of a complex number representing the corrected fluorescence data $A_2$.

The phase delay calculating unit 92 is a unit that calculates the argument of a complex number representing the corrected fluorescence data $A_1$ ($\tan^{-1}$(Im component of fluorescence data/Re component of fluorescence data)) as a phase delay $\theta$ and the argument of a complex number representing the corrected fluorescence data $A_2$ ($\tan^{-1}$(Im component of fluorescence data/Re component of fluorescence data)) as a phase delay $\theta$.

The fluorescence relaxation time calculating unit 94 is a unit that calculates a fluorescence relaxation time $\tau$ using the phase delay $\theta$ calculated by the phase delay calculating unit 92 according to the formula: $\tau=1/(2\pi f)\cdot\tan(\theta)$, where f is a frequency used to modulate the intensity of the laser beam $L_1$ or $L_2$. The reason why the fluorescence relaxation time $\tau$ can be calculated according to the formula: $\tau=1/(2\pi f)\cdot\tan(\theta)$ is that a fluorescence phenomenon shifts according to a first-order relaxation process.

The thus calculated fluorescence intensity, phase delay $\theta$, and fluorescence relaxation time $\tau$ are outputted as result information to a printer or display (not illustrated). The result information is measured every time the sample 12 passes through the measurement point in the tube 30 and used for statistical processing.

The flow cytometer 10 has such a structure as described above.

Hereinbelow, a method for detecting fluorescence using the flow cytometer 10 will be described.

First, laser beams $L_k$ of different wavelengths are prepared so as to correspond to fluorescent proteins $X_k$ so that the optical absorption of the fluorescent protein $X_k$ (k=1 or 2) becomes higher than that of the other fluorescent protein. The light source unit 22 modulates the intensities of the laser beams $L_k$ at different frequencies and emits these laser beams as one irradiation light to irradiate the fluorescent proteins $X_1$ and $X_2$ with the irradiation light.

Then, the light-receiving unit 26, which has wavelength bands $FL_k$ (k=1 or 2) set so as to correspond to the fluorescent proteins $X_k$ so that the fluorescence intensity of fluorescence emitted by the fluorescent protein $X_k$ becomes higher than that of fluorescence emitted by the other measurement object, receives fluorescence emitted by the fluorescent proteins $X_1$ and $X_2$ irradiated with the irradiation light and outputs fluorescent signals corresponding to the wavelength bands $FL_k$.

The control/processing unit 28 mixes each of the fluorescent signals outputted by the light-receiving unit 26 with a modulation signal for modulating the intensity of the laser beam $L_k$ (k=1) corresponding to the wavelength band $FL_k$ (k=1) to perform frequency-down conversion to produce data composed of a Re component and an Im component and containing the phase delay of the fluorescent signal with respect to the modulation signal and the intensity amplitude of the fluorescent signal.

The analyzing unit 83 of the analyzing device 80 further divides the data composed of a Re component and an Im component produced by the control/processing unit 28 into a DC component and a signal component with a frequency of $(f_2-f_1)$. The signal component with a frequency of $(f_2-f_1)$ is extracted by performing frequency-down conversion using a differential signal with a differential frequency of $(f_2-f_1)$ supplied from the signal generation unit 40. The DC component is extracted by performing FFT processing.

In this way, fluorescence data $A_1'$ composed of a Re component and an Im component and containing the phase delay of the fluorescent signal at a frequency of $f_1$ (the phase delay of the fluorescent signal with respect to the modulation signal with a frequency of $f_1$) and the intensity amplitude of the fluorescent signal is obtained. Further, fluorescence data $A_2'$ composed of a Re component and an Im component and containing the phase delay of the fluorescent signal at a frequency of $f_2$ (the phase delay of the fluorescent signal with respect to the modulation signal with a frequency of $f_2$) and the intensity amplitude of the fluorescent signal is obtained. The thus obtained fluorescence data $A_1'$ and fluorescence data $A_2'$ are corrected according to the above formula (3). Further, fluorescence data $A_1$ obtained by correcting the fluorescence data $A_1'$ and fluorescence data $A_2$ obtained by correcting the fluorescence data $A_2'$ are used to calculate a fluorescence intensity, a phase delay $\theta$, and a fluorescence relaxation time $\tau$.

It is to be noted that the flow cytometer 10 stores, in advance, the reference fluorescence data of the fluorescent protein $X_1$ containing a reference phase delay and a reference intensity amplitude obtained by measuring the fluorescent protein $X_1$ using the flow cytometer 10 and the reference fluorescence data of the fluorescent protein $X_2$ containing a reference phase delay and a reference intensity amplitude obtained by measuring the fluorescent protein $X_2$ using the flow cytometer 10, and performs correction according to the above formula (3) using a correction matrix calculated using the reference fluorescence data.

As described above, the analyzing unit 83 of the analyzing device 80 can remove unnecessary fluorescence data of fluorescence within the wavelength bands $FL_1$ and $FL_2$ before calculation of a fluorescence relaxation time $\tau$, which makes it possible to calculate a fluorescence relaxation time $\tau$ with high accuracy.

The flow cytometer 10 has been described above with reference to a case where the sample 12 is composed of a pair of biologically-bound cells that can cause FRET, but the sample 12 is not particularly limited as long as fluorescence is emitted by n (n is an integer of 2 or more) kinds of measurement objects. For example, n kinds of pairs of a first molecule and a second molecule that can cause FRET are used as measurement objects. Further, the measurement object that can cause FRET is not particularly limited as long as fluorochromes can pass through the measurement point at the same time.

Further, the control/processing unit 28 performs frequency-down conversion by mixing using the modulation signal with a frequency of $f_1$ as a first reference signal and then the analyzing device 80 performs frequency-down conversion using the differential signal with a differential frequency of $(f_2-f_1)$ as a second reference signal, but the control/processing unit 28 may perform frequency-down conversion by mixing using the modulation signal with a frequency of $f_1$ as a first reference signal and frequency-down conversion by mixing using the modulation signal with a frequency of $f_2$ as a first reference signal. In this case, the signal processing unit 42 is preferably configured so that the IQ mixer 58*a* can use the modulation signal with a frequency of $f_1$ as a first reference signal and the IQ mixer 58*b* can use the modulation signal with a frequency of $f_2$ as a first reference signal. This makes it possible to simultaneously determine a Re component and an Im component containing a phase delay and an intensity amplitude at a frequency of $f_1$ and a Re component and an Im component containing a phase delay and an intensity amplitude at a frequency of $f_2$ by using the IQ mixers 58a and 58b.

Although the fluorescence detecting device and the fluorescence detecting method according to the present invention have been described above in detail, the present invention is not limited to the above embodiment, and it should be understood that various changes and modifications may be made without departing from the scope of the present invention.

DESCRIPTION OF THE REFERENCE NUMERALS

- 10 flow cytometer
- 12 sample
- 20 signal processing device
- 22 laser light source unit
- 22a, 22b light source
- 23a, 26b dichroic mirror
- 23b, 26a lens system
- 24, 26 light-receiving unit
- 26c₁, 26c₂ band-pass filter
- 27a, 27b photoelectric converter
- 28 control/processing unit
- 30 tube
- 32 collection vessel
- 34a, 34b laser driver
- 48a, 48b power splitter
- 40 signal generation unit
- 42 signal processing unit
- 44 controller
- 46a, 46b oscillator
- 49, 62 low-pass filter
- 50a, 50b, 52, 54a, 54b, 64 amplifier
- 58a, 58b, 47 IQ mixer
- 60 system controller
- 66 AD converter
- 80 analyzing device
- 81 CPU
- 82 memory
- 83 analyzing unit
- 84 frequency analyzing unit
- 86 autofluorescence removing unit
- 88 fluorescence data correcting unit
- 90 fluorescence intensity calculating unit
- 92 phase delay calculating unit
- 94 fluorescence relaxation time calculating unit

The invention claimed is:

1. A device for detecting fluorescence by receiving fluorescence emitted by n (n is an integer of 2 or more) kinds of measurement objects irradiated with laser light and processing fluorescent signals of the received fluorescence, the device comprising:

a light source unit operable to modulate, at two or more different frequencies, intensities of laser beams $L_k$ (k is an integer of 1 to n) of different wavelengths prepared so as to correspond to measurement objects k so that optical absorption characteristics of each of the measurement objects are different from those of other one or more kinds of the measurement objects, and operable to output these laser beams $L_k$ as one irradiation light to irradiate the n kinds of measurement objects with the irradiation light;

a light-receiving unit that includes two or more light-receiving elements operable to receive fluorescence emitted by the n kinds of measurement objects irradiated with the irradiation light within wavelength bands $FL_k$ (k is an integer of 1 to n) set so as to correspond to the measurement objects k (k is an integer of 1 to n) so that fluorescence intensity of fluorescence emitted by each of the measurement objects is different from that or those of fluorescence emitted by other one or more kinds of the measurement objects, and operable to output fluorescent signals corresponding to the wavelength bands $FL_k$;

a first processing unit operable to perform frequency-down conversion by mixing each of the outputted fluorescent signals with a modulation signal for modulating at a least one of the intensities of the laser beams $L_k$ corresponding to the wavelength bands $FL_k$ (k is an integer of 1 to n) as a first reference signal to produce fluorescence data containing a phase delay and an intensity amplitude of each of the fluorescent signals; and a second processing unit operable to correct the produced fluorescence data and determine a phase delay of each of the fluorescent signals using the corrected fluorescence data, and to calculate a fluorescence relaxation time using the phase delay.

2. The fluorescence detecting device according to claim 1, wherein the second processing unit stores reference fluorescence data containing a reference phase delay and a reference intensity amplitude obtained by measuring the n kinds of measurement objects individually using the light-source unit, the light-receiving unit, and the first processing unit, and corrects the fluorescence data produced by the first processing unit with coefficients calculated by using the reference fluorescence data.

3. The fluorescence detecting device according to claim 1, wherein wavelength of each of the laser beams $L_k$ is set so that optical absorption of each of the measurement objects k (k is an integer of 1 to n) is higher than that of other one or more kinds of the measurement objects.

4. The fluorescence detecting device according to claim 1, wherein each of the wavelength bands $FL_k$ of the light-receiving unit is set so that a fluorescence intensity of fluorescence emitted by each of the measurement objects is higher than that or those of fluorescence emitted by other one or more of the measurement objects.

5. The fluorescence detecting device according to claim 4, wherein the reference fluorescence data is produced from the fluorescent signal of each of the measurement objects k outputted by the light-receiving element corresponding to a wavelength band $FL_m$ (m is an integer of 1 to n), the reference fluorescence data is represented as $a_{km} \cdot e^{(-i\theta_{km})}$ ($a_{km}$ is the reference intensity amplitude, $\theta_{km}$ is the reference phase delay), fluorescence data corresponding to the wavelength band $FL_m$ produced by the first processing unit is defined as $A_s'$ (s is an integer of 1 to n) represented by a complex number, and corrected fluorescence data is defined as $A_s$ (s is an integer of 1 to n) represented by a complex number, then $A_s$ is calculated from $A_s'$ according to a following formula (1):

Formula 1

$$\begin{Bmatrix} A_1 \\ A_2 \\ \vdots \\ A_n \end{Bmatrix} = \begin{bmatrix} 1 & \frac{a_{21}}{a_{22}}e^{-i(\theta_{21}-\theta_{22})} & \frac{a_{31}}{a_{33}}e^{-i(\theta_{31}-\theta_{33})} & \cdots \\ \frac{a_{12}}{a_{11}}e^{-i(\theta_{12}-\theta_{11})} & 1 & \frac{a_{32}}{a_{33}}e^{-i(\theta_{32}-\theta_{33})} & \cdots \\ \vdots & \vdots & \vdots & \\ \frac{a_{1n}}{a_{11}}e^{-i(\theta_{1n}-\theta_{11})} & \frac{a_{2n}}{a_{22}}e^{-i(\theta_{2n}-\theta_{22})} & \frac{a_{3n}}{a_{33}}e^{-i(\theta_{3n}-\theta_{33})} & \cdots \end{bmatrix}^{-1} \begin{Bmatrix} A_1' \\ A_2' \\ \vdots \\ A_n' \end{Bmatrix}. \quad (1)$$

6. The fluorescence detecting device according to claim 1, wherein
the second processing unit selects the fluorescence data as an object to be corrected, in a condition that the fluorescence data produced by the first processing unit is not within a predetermined range in a scatter diagram having a vertical axis representing a fluorescence intensity in one of two different wavelength bands and a horizontal axis representing a fluorescence intensity in another wavelength band, and
the fluorescence data is not selected as an object to be corrected, in a condition that the fluorescence data produced by the first processing unit is within the predetermined range.

7. The fluorescence detecting device according to claim 6, wherein each of the measurement objects is obtained by attaching a fluorochrome to a particle to be measured, and wherein the predetermined range is a range which corresponds to autofluorescence emitted by the particle to be measured and which is determined by measuring the particles having no fluorochrome attached thereto by using the fluorescence detecting device.

8. The fluorescence detecting device according to claim 1, wherein each of the measurement objects contains, as a pair, a first molecule and a second molecule that cause FRET (Fluorescence Resonance Energy Transfer) in which an energy of the first molecule is transferred to the second molecule, and the n kinds of measurement objects include two or more kinds of pairs of the first molecule and the second molecule.

9. The fluorescence detecting device according to claim 1, wherein
the first processing unit performs frequency-down conversion of each of the fluorescent signals using, as the first reference signal, a modulation signal for modulating one of the intensities of the laser beams $L_k$ corresponding to one of the wavelength bands $FL_k$ (k is an integer of 1 to n) defined as a first wavelength band, and further performs frequency-down conversion on a result of the frequency-down conversion using, as a second reference signal, a differential signal of a modulation signal of a frequency different from that of the first reference signal with respect to the first reference signal, to produce the fluorescence data containing the phase delay and the intensity amplitude.

10. A method for detecting fluorescence by receiving fluorescence emitted by n (n is an integer of 2 or more) kinds of measurement objects irradiated with laser light and processing fluorescent signals of the received fluorescence, the method comprising:
the first step of modulating, at two or more different frequencies, intensities of laser beams $L_k$ (k is an integer of 1 to n) of different wavelengths prepared so as to correspond to measurement objects k so that optical absorption characteristics of each of the measurement objects k (k is an integer of 1 to n) are different from those of other one or more kinds of the measurement objects and outputting these laser beams $L_k$ as one irradiation light to irradiate the n kinds of the measurement objects with the irradiation light;
the second step of receiving fluorescence emitted by the n kinds of measurement objects irradiated with the irradiation light within wavelength bands $FL_k$ (k is an integer of 1 to n) set so as to correspond to the measurement objects k (k is an integer of 1 to n) so that fluorescence intensity of fluorescence emitted by each of the measurement objects k is different from that or those of fluorescence emitted by other one or more kinds of the measurement objects and outputting fluorescent signals corresponding to the wavelength bands $FL_k$;
the third step of performing frequency-down conversion by mixing each of the outputted fluorescent signals with a modulation signal for modulating at a least one of intensities of the laser beams $L_k$ corresponding to the wavelength bands $FL_k$ (k is an integer of 1 to n) as a first reference signal, to produce fluorescence data containing a phase delay and an intensity amplitude of each of the fluorescent signals; and
the fourth step of correcting the produced fluorescence data, determining a phase delay of each of the fluorescent signals using the corrected fluorescence data, and calculating a fluorescence relaxation time using the phase delay.

11. The fluorescence detecting method according to claim 10, wherein the correction of the fourth step is performed by using a matrix calculated using previously-stored reference fluorescence data which is obtained by measuring the n kinds of measurement objects individually by performing the first, second, and third steps and which contains a reference phase delay and a reference intensity amplitude.

12. The fluorescence detecting method according to claim 10, wherein the wavelength of each of the laser beams $L_k$ is set so that optical absorption of each of the measurement objects k (k is an integer of 1 to n) is higher than that of other one or more kinds of the measurement objects.

13. The fluorescence detecting method according to claim 10, wherein each of the wavelength bands $FL_k$ is set so that a fluorescence intensity of fluorescence emitted by each of the measurement objects is higher than that or those of fluorescence emitted by other one or more kinds of the measurement objects.

14. The fluorescence detecting method according to claim 13, wherein
the reference fluorescence data is produced from the fluorescent signal of each of the measurement objects k outputted by the light-receiving element corresponding to a wavelength band $FL_m$ (m is an integer of 1 to n),
the reference fluorescence data is represented as $a_{km} \cdot e^{(-i\theta_{km})}$ ($a_{km}$ is the reference intensity amplitude, $\theta_{km}$ is the reference phase delay),
fluorescence data corresponding to the wavelength band $FL_m$ produced by the first processing unit is defined as $A_s'$ (s is an integer of 1 to n) represented by a complex number, and corrected fluorescence data is defined as $A_s$ (s is an integer of 1 to n) represented by a complex number, then $A_s$ is calculated from $A_s'$ according to the following formula (1):

Formula 2

$$\begin{Bmatrix} A_1 \\ A_2 \\ \vdots \\ A_n \end{Bmatrix} = \begin{bmatrix} 1 & \frac{a_{21}}{a_{22}}e^{-i(\theta_{21}-\theta_{22})} & \frac{a_{31}}{a_{33}}e^{-i(\theta_{31}-\theta_{33})} & \cdots \\ \frac{a_{12}}{a_{11}}e^{-i(\theta_{12}-\theta_{11})} & 1 & \frac{a_{32}}{a_{33}}e^{-i(\theta_{32}-\theta_{33})} & \cdots \\ \vdots & \vdots & \vdots & \\ \frac{a_{1n}}{a_{11}}e^{-i(\theta_{1n}-\theta_{11})} & \frac{a_{2n}}{a_{22}}e^{-i(\theta_{2n}-\theta_{22})} & \frac{a_{3n}}{a_{33}}e^{-i(\theta_{3n}-\theta_{33})} & \cdots \end{bmatrix}^{-1} \begin{Bmatrix} A_1' \\ A_2' \\ \vdots \\ A_n' \end{Bmatrix}. \quad (1)$$

15. The fluorescence detecting method according to claim 10, wherein the third step includes frequency-down conversion of each of the fluorescent signals using, as the first reference signal, a modulation signal for modulating one of the intensities of the laser beams $L_k$ corresponding to one of the wavelength bands $FL_k$ (k is an integer of 1 to n) defined as a first wavelength band, and further includes another frequency-down conversion on a result of the frequency-down conversion using, as a second reference signal, a differential signal of a modulation signal of a frequency different from that of the first reference signal with respect to the first reference signal, to produce the fluorescence data containing the phase delay and the intensity amplitude.

* * * * *